(12) United States Patent
Ghazwani

(10) Patent No.: US 11,002,721 B2
(45) Date of Patent: May 11, 2021

(54) AUTOMATED ORGANIC PETROLOGY

(71) Applicant: Saudi Arabian Oil Company, Dhahran (SA)

(72) Inventor: Assad Hadi Ghazwani, Bahrain (SA)

(73) Assignee: Saudi Arabian Oil Company, Dhahran (SA)

(*) Notice: Subject to any disclaimer, the term of this patent is extended or adjusted under 35 U.S.C. 154(b) by 165 days.

(21) Appl. No.: 16/280,860

(22) Filed: Feb. 20, 2019

(65) Prior Publication Data

US 2020/0264152 A1 Aug. 20, 2020

(51) Int. Cl.
*G01N 33/24* (2006.01)
*G01N 21/64* (2006.01)
*G01N 35/00* (2006.01)

(52) U.S. Cl.
CPC ......... *G01N 33/24* (2013.01); *G01N 21/6458* (2013.01); *G01N 35/00722* (2013.01)

(58) Field of Classification Search
CPC .............. G01N 33/24; G01N 33/241; G01N 35/00722; G16C 20/30; G16C 20/70
See application file for complete search history.

(56) References Cited

U.S. PATENT DOCUMENTS

| | | | | | |
|---|---|---|---|---|---|
| 4,814,614 | A | * | 3/1989 | Tsui | E21B 49/005 250/255 |
| 2010/0105975 | A1 | * | 4/2010 | Baird | E21B 41/0057 588/16 |
| 2013/0064040 | A1 | * | 3/2013 | Imhof | G01V 1/302 367/73 |
| 2017/0226851 | A1 | | 8/2017 | Hakami et al. | |
| 2018/0031732 | A1 | * | 2/2018 | Mosse | G01V 99/005 |
| 2018/0347354 | A1 | * | 12/2018 | Li | G01N 33/241 |

FOREIGN PATENT DOCUMENTS

CN 102928340 2/2013

OTHER PUBLICATIONS

PCT International Search Report and Written Opinion in International Appln. No. PCT/US2020/019008, dated Jun. 16, 2020, 24 pages.

Ayling et al., "QEMSCAN (Quantitative Evaluation of Minerals by Scanning Electron Microscopy): Capability and Application to Fracture Characterization in Geothermal Systems," proceedings of the Thirty-Seventh Workshop on Geothermal Reservoir Engineering, Stanford University, Stanford, California, Jan. 30-Feb. 1, 2012, 11 pages.

Berry et al., "Automated Mineral Identification by Optical Microscopy," Ninth Internaitonal Congress for Applied Mineralogy, Sep. 8-10, 2008, 5 pages.

(Continued)

*Primary Examiner* — Ross Varndell
(74) *Attorney, Agent, or Firm* — Fish & Richardson P.C.

(57) ABSTRACT

A photomicrograph of a rock sample is analyzed. One or more classification attributes of the photomicrograph are recorded. One or more maceral attributes of the photomicrograph are determined using automated face detection. Based on the one or more classification attributes and the one or more maceral attributes, one or more technical attributes of the photomicrograph are determined using automated face recognition. The one or more maceral attributes and the one or more technical attributes are provided.

14 Claims, 17 Drawing Sheets

(56) References Cited

OTHER PUBLICATIONS

Suarez-Ruiz et al., "Review and update of the applications of organic petrology: Part 1, Geological applications," International Journal of Coal Geology, vol. 99, Sep. 1, 2012, 59 pages.

Valentine et al., "Development of web-based organic petrology photomicrograph atlases and internet resources for professionals and students," International Journal of Coal Geology, vol. 111, May 2013, 6 pages.

\* cited by examiner

AUTOMATED ORGANIC PETROLOGY

TECHNICAL FIELD

This disclosure relates to automation as it is applied to organic petrology.

BACKGROUND

Commercial-scale hydrocarbon production from source rocks and reservoirs requires significant capital. It is therefore beneficial to obtain as much accurate data as possible about a formation in order to assess its commercial viability and subsequently to optimize cost and design of development. Organic petrological and geochemical investigations are examples of suitable methods to obtain data. Attributes of depositional environments, types and richness of organic matter, and the level of thermal maturity in a sedimentary basin are a few examples of data that can be obtained from such investigations.

SUMMARY

This disclosure describes technologies relating to automation as it is applied to organic petrology.

Certain aspects of the subject matter described can be implemented as a method. One or more classification attributes of a photomicrograph of a rock sample are recorded. The one or more classification attributes include region of origin, basin, age, depth, lithology, stratigraphic unit, standard of preparation, or combinations of these. One or more maceral attributes of the photomicrograph are determined using automated face detection. Determining the one or more maceral attributes of the photomicrograph includes measuring a vitrinite reflectance of the photomicrograph to determine a presence of vitrinite in the rock sample. Based on the one or more classification attributes and the one or more maceral attributes, one or more technical attributes of the photomicrograph are determined using automated face recognition. The one or more technical attributes include thermal maturity, organic richness, mineral composition, or combinations of these. Determining the one or more technical attributes includes comparing results of the automated face detection to a database of photomicrographs with overlap in one or more classification attributes. The one or more maceral attributes and the one or more technical attributes are provided.

This, and other aspects, can include one or more of the following features.

The photomicrograph can include an incident light photomicrograph of the rock sample.

The incident light photomicrograph of the rock sample can be obtained.

Determining the one or more maceral attributes of the photomicrograph can include determining whether vitrinite suppression has occurred in the rock sample.

The photomicrograph of the rock sample can be a set of photomicrographs of the rock sample. The set can include an incident light photomicrograph of the rock sample and a fluorescent photomicrograph of the rock sample.

The fluorescent photomicrograph of the rock sample can be obtained in response to determining that vitrinite suppression has occurred in the rock sample.

A presence of macerals other than vitrinite in the rock sample can be determined using automated face detection on the fluorescent photomicrograph.

A total organic content of the rock sample can be measured in weight percent.

Determining the one or more technical attributes of the photomicrograph can include identifying one or more minerals that make up the total organic content of the rock sample.

Certain aspects of the subject matter described can be implemented as a system for automated organic petrology. The system includes a memory and a hardware processor interoperably coupled with the memory. The hardwire processor is configured to record one or more classification attributes of a photomicrograph of a rock sample. The one or more classification attributes include region of origin, basin, age, depth, lithology, stratigraphic unit, standard of preparation, or combinations of these. The hardwire processor is configured to determine one or more maceral attributes of the photomicrograph using automated face detection. Determining the one or more maceral attributes of the photomicrograph includes measuring a vitrinite reflectance of the photomicrograph to determine a presence of vitrinite in the rock sample. The hardwire processor is configured to determine one or more technical attributes of the photomicrograph are determined using automated face recognition based on the one or more classification attributes and the one or more maceral attributes. The one or more technical attributes include thermal maturity, organic richness, mineral composition, or combinations of these. Determining the one or more technical attributes includes comparing results of the automated face detection to a database of photomicrographs with overlap in one or more classification attributes. The hardwire processor is configured to provide the one or more maceral attributes and the one or more technical attributes.

This, and other aspects, can include one or more of the following features.

The hardwire processor can be configured to obtain an incident light photomicrograph of the rock sample.

The hardwire processor can be configured to determine whether vitrinite suppression has occurred in the rock sample.

The hardware processor can be configured to obtain a fluorescent photomicrograph of the rock sample in response to determining that vitrinite suppression has occurred in the rock sample.

The hardware processor can be configured to determine a presence of macerals other than vitrinite in the rock sample using automated face detection on the fluorescent photomicrograph.

The hardware processor can be configured to measure a total organic content of the rock sample in weight percent.

The hardware processor can be configured to identify one or more minerals that make up the total organic content of the rock sample.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes utilizing automation in the field of organic petrology. Automated face detection and face recognition can be used to identify and classify rock samples gathered from hydrocarbon-containing subterranean zones (conventional and unconventional, alike) and to establish organic petrological and geochemical correlations and characterizations. The information gathered from such automated processes can be used, for example, to determine the viability of drilling a well in an unexplored basin. The subject matter described in this disclosure can be implemented in particular implementations, so as to realize one or more of the following advantages. Using face detection and face recognition, various attributes of a rock sample can be determined, such as thermal maturity, organic richness, maceral type, and mineralogy. An incident light analysis and reflectance measurements can be performed to determine the presence of vitrinite in rock samples. If no vitrinite is detected, a fluorescence analysis can be performed to identify different maceral types in rock samples. Various photomicrograph attributes can be determined by comparing information about the rock sample with a database of rock attributes, such as region of origin, sedimentary basin, age, depth of source rock, lithology, stratigraphic unit, and sample preparation methods. The gathered information can be added to an existing database of photomicrographs of hydrocarbon basins located worldwide. Adding this gathered information can in turn also improve the recognition capability of the automated face recognition. Thermal maturity and organic richness trends and correlations of various hydrocarbon basins can be generated from the gathered information.

Figure 1:
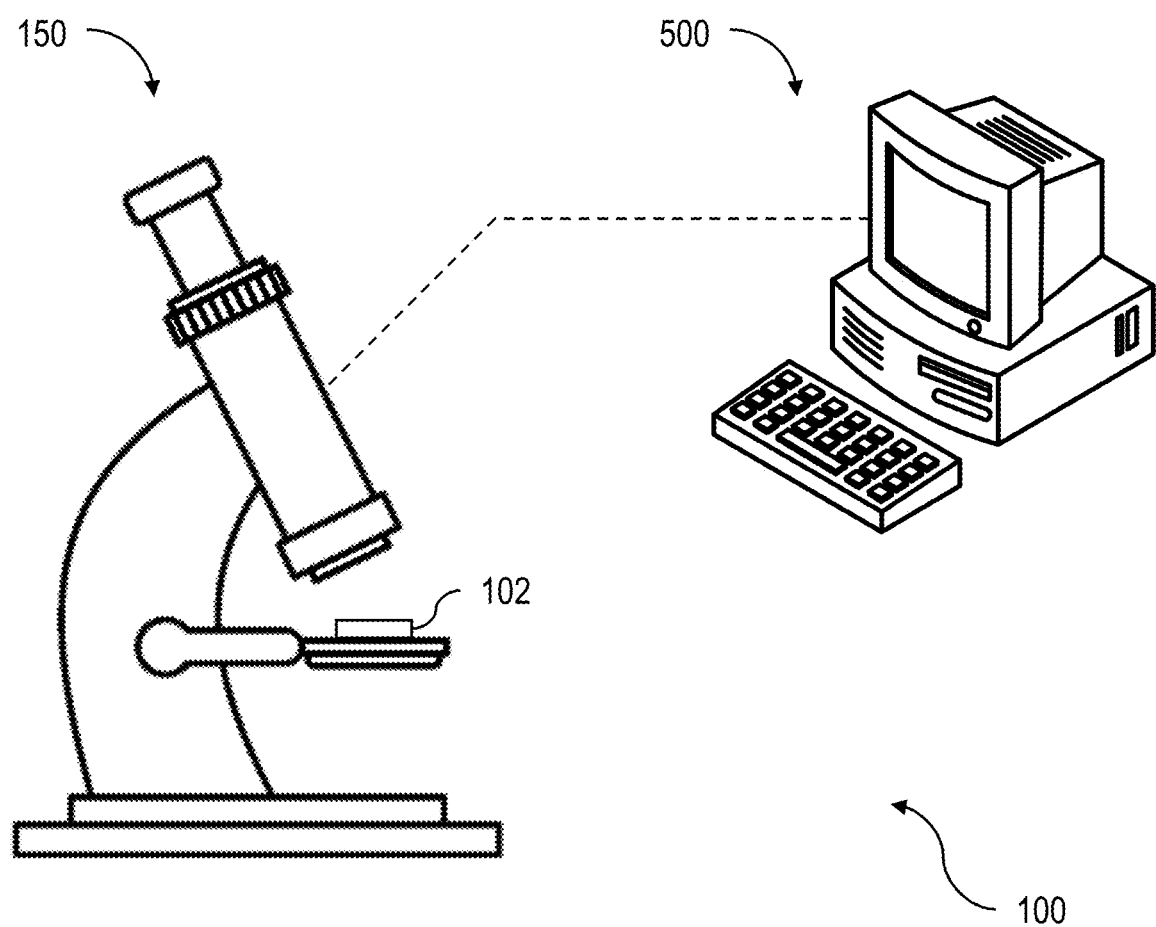
FIG. 1 is a schematic diagram of an exemplary system for automated organic petrology.

FIG. 1 illustrates an example system 100 that can be used to implement automated face detection and automated face recognition to identify attributes of and classify a rock sample 102. The system 100 includes an optical microscope 150 and a computer 500. The microscope 150 includes a light source, a magnifier, and a camera. The microscope 150 can use fluorescence or phosphorescence (or both) instead of, or in addition to, reflection and absorption to study properties of the rock sample 102. In such implementations, the microscope 150 can include a xenon arc lamp, a mercury-vapor lamp with an excitation filter, a laser, a supercontinuum source, a high-power light-emitting diode (LED), or combinations of these. The computer 500 can be connected to the microscope 150 and can be configured to control various operations of the microscope 150. For example, the computer 500 can be used to control the camera of the microscope 150. A photomicrograph captured by the camera can be viewed and stored on the computer 500. The computer 500 can be configured to process the photomicrograph and perform the automated face detection and automated face recognition to identify attributes of and classify the rock sample 102. The automated face detection and automated face recognition can include comparing the photomicrograph captured by the camera to other photomicrographs, for example, available from one or more databases of photomicrographs of rock samples from various basins around the world.

Figure 2:
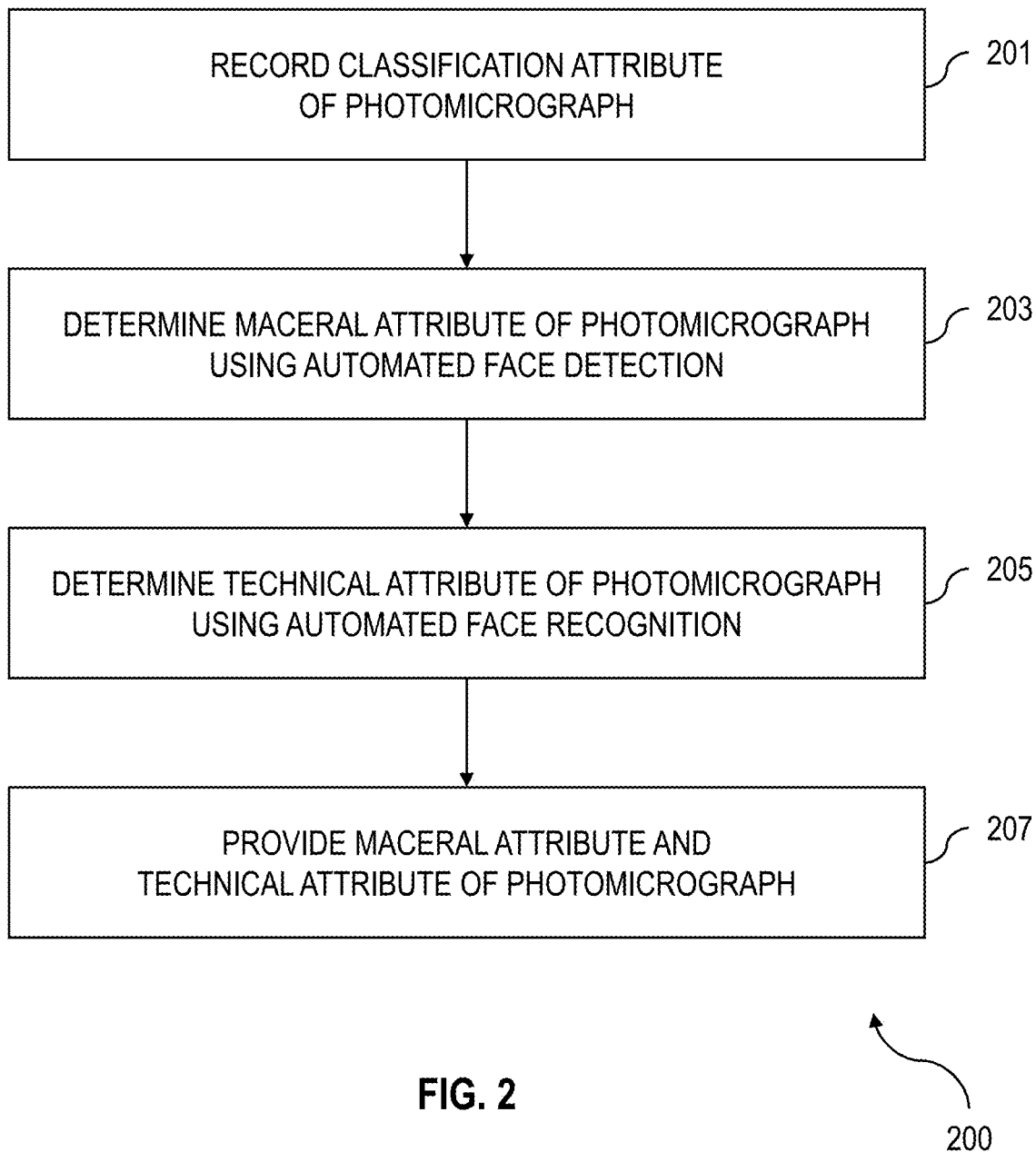
FIG. 2 is a flow chart of an exemplary method for using the system of FIG. 1.

FIG. 2 is a flow chart illustrating an example method 200 for identifying attributes of and classifying a rock sample (such as the rock sample 102). The system 100 can be used to implement the method 200. A photomicrograph of the rock sample 102 is obtained. The photomicrograph can be obtained using the microscope 150 and the computer 500. The photomicrograph can be an incident light photomicrograph. In some implementations, the photomicrograph is a fluorescence or phosphorescence photomicrograph. Before obtaining the photomicrograph, the rock sample 102 can be prepared according to an industry standard (some examples of industry standards of rock sample preparation are listed later). Care can be taken to avoid introducing moisture during rock sample preparation.

At step 201, one or more classification attributes of the photomicrograph are recorded. The one or more classification attributes can include region of origin, basin, age, depth, lithology, stratigraphic unit, standard of preparation, or combinations of these. Some non-limiting examples of region of origin include United States of America, Canada, South America, Northern and Western Europe, Eastern Europe, Caspian, North Africa, Sub-Saharan Africa, Middle East, Asia, Australia, and New Zealand.

Some non-limiting examples of basins in the United States of America include the Permian Basin of West Texas and Southeastern New Mexico; the Fort Worth Basin of Texas; the Gulf of Mexico Basin; the Western Gulf Basin of South Texas; the Arkoma Basin of Arkansas; the Salt Basin of Texas and Louisiana; the Appalachian Basin; the Anadarko Basin of Oklahoma and Texas; the Ardmore Basin of Oklahoma and Texas; the Williston Basin of North Dakota, Montana, Saskatchewan, and Manitoba; the Black Warrior Basin; the Denver Basin; the Eastern Great Basins; the Powder River Basin; the Great Green River Basin; the Paradox-San Juan Basin; and the Ventura Basin.

Some non-limiting examples of basins in Canada include the Horn River Basin; the Williston Basin of Saskatchewan, and Manitoba; the Cordova Basin; the Liard Basin; the Doig Phosphate Deep Basin; the Alberta Basin; the Northwest Alberta Basin; the East and West Shale Basin; the Southern Alberta Basin; the Appalachian, Quebec Basin; the Windsor Basin; and the Moncton sub-Basin and Maritimes Basin.

Some non-limiting examples of basins in South America include the Neuquen Basin of Argentina; the San Jorge Basin of Argentina; the Austral-Magallanes Basin of Argentina and Chile; the Parana Basin of Argentina, Paraguay, Uruguay, and Brazil; the Chaco Basin of Paraguay and Bolivia; the Solimões Basin of Brazil; the Amazonas Basin of Brazil; the Middle Magdalena Valley Basin of Colombia; the Llanos Basin of Colombia; the Maracaibo/Catatumbo Basin of Venezuela and Colombia; and the Putamayo Basin.

Some non-limiting examples of basins in Northern and Western Europe include the Paris Basin of France; the South-East Basin of France; the Lower Saxony Basin of Germany; the West Netherland Basin of the Netherlands; the Basque-Cantabrian Basin of Spain; the Ebro Basin of Spain; the Greater Pennine Basin of England; the Wessex Basin of England; and the Weald Basin of England.

Some non-limiting examples of basins in Eastern Europe include the Dnieper-Donets Basin of Ukraine; the Carpathian Basin of East Ukraine; the Moesian Basin of Romania and Bulgaria; the Fore-Sudetic Basin of Poland; the West Siberian Basin of Russia; the East Siberian Basin of Russia; the Southeast Anatolian Basin of Turkey; and the Thrace Basin of Turkey.

Some non-limiting examples of basins in the Caspian include the North Caspian Basin of Kazakhstan; the Mangyshlak Basin of Kazakhstan; the South Turgay Basin of Kazakhstan; the Chu-Sarysu Basin of Kazakhstan; and the North Ustyurt Basin of Kazakhstan.

Some non-limiting examples of basins in North Africa include the Ghadames/Berkine (Upper Devonian) Basin of Algeria; the Timimoun (Upper Devonian) Basin of Algeria; the Ahnet (Upper Devonian) Basin of Algeria; the Reggane (Upper Devonian) Basin of Algeria; the Ghadames/Berkine (Upper Devonian) Basin of Libya; the Sirte Basin of Libya; the Tripolitanian Offshore Basin of Libya; the Kufra Basin of Libya; the Ghadames Basin of Tunisia; the Pelagian Basin of Tunisia; the Tindouf (Devonian) Basin of Morocco; the Abu Gharadig Basin of Egypt; the Alamein Basin of Egypt; the Natrun Basin of Egypt; the Shoushan-Matruh Basin of Egypt; the Nile Delta and North Sinai Basins of Egypt; the Gindi Basin of Egypt; the Gulf of Suez Basin of Egypt; the Kom Ombo Basin of Egypt; and the Levantine Basin of Egypt.

Some non-limiting examples of basins in Sub-Saharan Africa include the Termit Basin of Chad; the Bongor Basin of Chad; the Doba Basin of Chad; the Doseo Basin of Chad; and the Karoo Basin of South Africa.

Some non-limiting examples of basins in the Middle East include the North Oman Basin of Oman; the Rub Al-Khali Basin of United Arab Emirates; the Mesopotamian Basin of Iraq; the Dead Sea Basin of Jordan; the Levantine Basin of Lebanon; the Palmyride Basin of Lebanon; the Levantine Basin of Israel; the Dead Sea Basin of Israel; the Kopet Dagh Basin of Iran; the Central Iran Basin of Iran; and the Alborz Basin of Iran.

Some non-limiting examples of basins in Asia include the Sichuan Basin of China; the Yangtze Basin of China; the Jianghan Basin of China; the Greater Subei Basin of Chine; the Tarim Basin of China; the Junggar Basin of China; the Songliao Basin of China; the Cambay Basin of India and Pakistan; the Krishna-Godavari Basin of India; the Cauvery Basin of India; the Damodar Valley Basin of India; the Lower Indus Basin of Pakistan; the Upper Assam Basin of India; the Pranhita-Godavari Basin of India; the Vindhyan Basin of India; the Rajasthan Basin of Pakistan; the Central Sumatra Basin of Indonesia; the South Sumatra Basin of Indonesia; the Kutai Basin of Indonesia; the Tarakan Basin of Indonesia; the Bintuni Basin of Indonesia; the East Gobi Basin of Mongolia; the Tamtsag Basin of Mongolia; the Hailaer Basin of Mongolia; the Khorat Basin of Thailand; the Central Plains Basin of Thailand; and the Northern Intermontane Basin of Thailand.

Some non-limiting examples of basins in Australia include the Cooper Basin; the Maryborough Basin; the Perth Basin; the Canning Basin; the Georgina Basin; and the Beetaloo Basin.

Some non-limiting examples of basins in New Zealand include the Taranaki Basin; the Wanganui Basin; the Deep Taranaki Basin; the East-West Coast Basin; the Raukumara Basin; the Northland Basin; the North Slope Basin; the Bellona Basin; the Fiordland Basin; the West South Solander Basin; the Great South Basin; and the Chatham Slope Basin.

The rock sample 102 can be classified, for example, as pre-Devonian, Devonian, or younger than Devonian. An age of more than approximately 419.2 million years can be considered pre-Devonian. An age of between approximately 419.2 million years and approximately 358.9 million years can be considered Devonian. An age younger than approximately 358.9 million years can be considered younger than Devonian. In some implementations, Devonian age rock samples can be further categorized as Upper, Middle, or Lower Devonian. For pre-Devonian age rock samples, vitrinite reflectance and fluorescence may not be applicable because the vascular plants from which the macerals are derived did not yet evolve to exist in such time periods.

The rock sample 102 can be attributed to a depth within a subterranean zone from which the rock sample 102 was obtained. For example, the rock sample 102 can be attributed to a depth between 0 feet (at the surface) and approximately 20,000 feet. Sedimentary basins can have various regions of differing thermal maturities. For example, in young, near-surface sediments, vitrinite reflectance can, in some cases, be as low as 0.2% $R_o$ and can increase with increasing depth and temperature (in some cases, increasing to greater than 4% $R_o$). In some cases, older sediments located near the surface can also low thermal maturity with low vitrinite reflectance (for example, 0.37% $R_o$). Table 1 shows a few examples of rock samples at varying ages and depths, along with their vitrinite reflectance measurements.

TABLE 1

| Age | Depth (meters) | Stratigraphic Unit | Vitrinite Reflectance (% $R_o$) |
|---|---|---|---|
| Oligocene | 104 | Silesian | 0.32 |
| Devonian | 10 | Flagstone | 0.53 |
| Carboniferous | 68.6 | Zieglschiefer | 1.8 |
| Carboniferous | 32 | Upper Alum Shale | 2.33 |
| Carboniferous | 53 | Lower Alum Shale | 2.80 |

Regarding lithology, the rock sample 102 can be obtained, for example, in the form of small chips of slabbed cores, core plugs, or cuttings. In some implementations, the source rock from which the rock sample 102 is obtained contains sufficient organic content (for example, at least about 2 weight % total organic content) and is siltstone, marlstone, or shale. The lithological characteristics of the rock sample 102 can include color, texture, grain size, composition (for example, mineralogy or organic content), or combinations of these. Table 2 shows a few examples of rock samples of various origins, along with their total organic content (TOC).

TABLE 2

| Source Rock | Country | TOC (weight %) |
|---|---|---|
| Lower Alum Shale | Germany | 2.5 |
| Upper Alum Shale | Germany | 2.8 |
| Woodford Shale | United States | 4 |
| Barnett Shale | United States | 4.8 |

The stratigraphic unit of the rock sample 102 can be related to age of the rock sample 102 and the depth within the subterranean zone from which the rock sample 102 was obtained. The stratigraphic unit of the rock sample 102 can also be related to the region of origin and basin from which the rock sample 102 was obtained.

The rock sample 102 can be classified based on the method of preparation of the rock sample 102. Some non-limiting examples of methods of preparing the rock sample 102 include an International Committee for Coal and organic Petrography (ICCP) method, an American Society for Testing and Materials (ASTM) method, a German Institute for Standardization (DIN) method, a Standard Association of Australia (SAA) method, a Commonwealth Scientific and Industrial Research Organization (CSIRO) method, a Single Coal Accreditation Program (SCAP) method, a Dispersed Organic Matter Vitrinite Reflectance Accreditation (DOMVR) method, a Coal Blends Accreditation Program (CBAP) method, and an Australian Coal Industrial Research Laboratories (ACIRL) Ltd. method.

In some implementations, the photomicrograph can be indexed by the various classification attributes (such as region of origin, basin, age, depth, lithology, stratigraphic unit, and method of preparation) recorded at step 201. This indexing can aid the face detection and face recognition processes in determining characteristics of the rock sample 102 and comparing the characteristics of the rock sample 102 to those already existing in a database.

At step 203, one or more maceral attributes of the photomicrograph are determined using automated face detection. A vitrinite reflectance of the photomicrograph can be measured to determine a presence of vitrinite in the rock sample 102. Vitrinite is a component of coals and various sedimentary kerogens. Vitrinite is a type of maceral, where macerals are the organic components of coal analogous to the minerals of rocks. Vitrinite is derived from the cell-wall material or woody tissue of plants from which coal was formed and typically has a shiny appearance resembling glass. Incident light can determine the presence of vitrinite. Vitrinite's refractive and absorptive indices are direct functions of a degree of aromatization and abundance of delocalizing electrons. The rock sample 102 can be polished and immersed in oil, and the camera of the microscope 150 can capture the photomicrograph at, for example, 400 to 750 times magnification under incident white light. The reflected light from the vitrinite can be calibrated to standards of photomicrographs with known reflectance values, and the vitrinite reflectance can be recorded as a percentage value (% $R_o$). Vitrinite reflectance can be correlated to hydrocarbon maturity. For example, vitrinite reflectance of about 0.2% $R_o$ to about 0.6% $R_o$ can be attributed to an "immature" hydrocarbon maturity stage; vitrinite reflectance of about 0.6% $R_o$ to about 1.3% $R_o$ can be attributed to a "mature" hydrocarbon maturity stage; vitrinite reflectance of about 1.3% $R_o$ to about 2.0% $R_o$ can be attributed to a "post-mature" hydrocarbon maturity stage; and vitrinite reflectance of about 2.0% $R_o$ and greater can be attributed to an "over-mature" hydrocarbon maturity stage.

The vitrinite can be distinguished from other organic matter that sometimes appear similar to vitrinite. For example, solid bitumen can be recognized by its fracture filling, groundmass, and void-filling textures, along with its typically low-gray reflecting surface. A low-gray reflecting texture occurring with plant cellular structures can help to distinguish solid bitumen from, for example, terrestrial type III kerogen vitrinite. Graptolite can be distinguished from other types of organic matter due to its typically granular surface, for example, occurring in a carbonate matrix with low reflectance and bireflectance. Bireflectance is an optical effect where a mineral (or organic material) appears to change in intensity as the sample is rotated while illuminated by plane-polarized light. Graptolite with a non-granular surface, for example, occurring in a shale matrix can have high reflectance and bireflectance. The bireflectance of graptolite can be used to differentiate graptolite from vitrinite and other maceral types.

In some implementations, vitrinite is absent in the rock sample 102. In such cases, the fluorescence or phosphorescence photomicrograph can be used. Liptinite is a type of maceral which can be identified with fluorescence. Liptinite is derived from spores, pollen, dinoflagellate cysts, leaf cuticles, plant resins and waxes, or combinations of these. Liptinite typically auto-fluoresces when illuminated with ultraviolet or blue light and can be identified by its distinct shape. For example, alginate (a type of liptinite) typically occurs in discrete bodies (in the case of telalginite) or lamellar masses (in the case of lamalginite). Liptinite can also be distinguished from other maceral types by its lower reflectance and high hydrogen content. In some cases, the properties of liptinite can be similar to those of vitrinite (for example, 1.3% $R_o$ to 14% $R_o$ based on the characteristics of the coal).

Some non-limiting examples of macerals in the liptinite group include cutinite, suberinite, sporinite, resinite, exsudatinite, chlorophyllinite, alginate, liptodetrinite, and bituminite. The various liptinite macerals can have different thermal maturities. For example, suberinite, bituminite, and resinite can generate petroleum at low reflectance (such as about 0.4% $R_o$), and cutinite and alginite can generate petroleum at higher reflectance (such as about 0.7% $R_o$ to about 0.8% $R_o$).

Liptinite typically appears dark gray to black when illuminated with white light. Liptinite reflectance can increase with increasing maturity. In transmitted light (backlight illumination), liptinite can appear yellow to brownish red. In fluorescence, liptinite can appear greenish yellow at low rank to orange at a higher rank. Coal can be classified based on rank, which is the degree of coalification that has occurred. The rank of coal can be determined by depth of burial and temperature to which the coal was subjected over time. For example, soft brown coal can be classified as "low rank", sub-bituminous coal can be classified as "medium rank", and anthracite can be classified as "high rank". Fluorescence intensity of liptinite can decrease with increasing maturity. The following describes various types of liptinite.

Cutinite is a fossil organic constituent derived from cuticles of leaves and stems. In reflected light, cutinite can appear dark gray to black with a red cast in some parts. Cutinite can sometimes have an orange-colored internal reflection. In fluorescence, cutinite can appear greenish yellow to orange.

Suberinite is coalified cell wall derived from suberized cell walls. In polished sections, suberinite tissue (especially cork tissue) can have a succession of rectangular, brick-like, or irregular, 4- to 6-sided polygonal cells. In reflected light, suberinite can appear medium gray to black. In fluorescence, suberinite can appear light blue to greenish yellow, orange, or brown. The color of suberinite can depend on the degree of coalification of the suberinite. Suberinite can be found in small amounts in all types of coal and can have a waxy, oily chemical makeup.

Sporinite is derived from exines and perines of plant spores and pollens. The size of sporinite can vary from approximately 10 micrometers (μm) to 2,000 μm. Sporinite of thick-walled megaspores is typically granular. Sporinite of microspores and pollen grains is typically compact and homogenous. In reflected light, sporinite can appear rusty brown, dark gray, and occasionally black at low maturity. With increasing maturity, sporinite can, in some cases, appear light gray and appear similar to vitrinite. In fluorescence, the color of sporinite is dependent on its level of thermal maturity. Fluorescence intensity of sporinite can increase with increasing maturity. At low maturities, sporinite can have a higher resistance to polishing than vitrinite. Polishing hardness (that is, resistance to polishing) can vary depending on the origin of the maceral and coal rank. For example, sporinite can have a high resistance to polishing due to its softness and elasticity at low rank. As another example, bituminite at low rank can be softer in comparison to sporinite with respect to polishing, meaning it can be difficult to polish (for example, bituminite can smear when subjected to a polishing process).

Resinite is derived from resins and waxes occurring, for example, as discrete bodies of varying shapes, such as round, oval, or rod-like in cross-sections or as diffuse impregnation resin. In reflected light, resinite can appear black to dark gray with lighter gray external zones at low maturity. Resinite can often have yellow, orange, or red internal reflections. In fluorescence, resinite can appear blue to green. With blue light excitation, resinite can appear yellow or orange to light brown.

Exsudatinite (also known as exudatinite) is a secondary maceral that can be generated during coalification. Exsudatinite is solid residue of an originally petroleum-like, commonly asphaltic nature. Exsudatinite can exceed the typical reflectance of vitrinite. Exsudatinite can also exhibit a higher degree of anisotropy than vitrinite of the same maturity. Anisotropy in coal can be linked to pressure that generally rises with increasing coal rank and structure of the carbonaceous material. Anisotropy can be a result of an asymmetry of line and shape of the molecular structure with an axial symmetry. Oxidation can damage the coking properties of coal and activate carbon with high isotropy and anisotropy. Anisotropy can be identified, for example, through visual properties that are parallel or perpendicular to aromatic layers which can gradually become apparent. Reflectivity and refractive index can represent such changes determined by the internal structure of the coal. In fluorescence, exsudatinite can appear different in color and intensity from the source maceral. With respect to polishing, exsudatinite can be soft and elastic at low maturity.

Chlorophyllinite is typically in the form of small, round particles approximately 1 to 5 µm in size. In reflected light, chlorophyllinite can have a weak reflectance and is sometimes difficult to distinguish from liptodetrinite. In fluorescence, chlorophyllinite can appear a deep red.

Alginite can be derived from unicellular (solitary) or colonial algae of planktonic and benthic origin. Telalginite (a type of alginite) is typically in the form of discrete lenses, fan-shaped masses, or flattened disks, all of which can have a distinctive external form and in most cases, internal form. In reflected light, telalginite can appear dark in relation to sporinite. Alginite reflectance can increase with increasing maturity (typically 0.8% $R_o$ in contrast to typical vitrinite reflectance 1.1% $R_o$). In reflected light, telalginite can appear green due to auto-fluorescence. In transmitted light, telalginite can appear pale yellow to brown, depending on its maturity level. In fluorescence, telalginite is typically associated with low vitrinite reflectance values (due to suppression). For example, torbanite can exhibit low vitrinite reflectance values (such as about 0.33% $R_o$ to about 0.75% $R_o$). Samples with high alginate content can be subject to vitrinite suppression (thereby lowering vitrinite reflectance values).

Liptodetrinite is derived from small particles of spores, pollen cuticles, resins, waxes, cutinized and suberinized cell walls. Liptodetrinite is typically abundant when other liptinite macerals are strongly represented in the sample. Liptodetrinite can have fluorescing constituents that are a few µm in size, varying from rodlets, sharp-edged splinters, threadlike structures, and round particles. The size and shape of liptodetrinite particles of low thermal maturity can typically be distinguished by the use of fluorescence microscopy. In reflected light, liptodetrinite can appear black, dark gray, or brown. Liptodetrinite can have dense layers of brown or red internal reflections. In transmitted light, liptodetrinite can appear reddish-yellow. In fluorescence, liptodetrinite can appear greenish yellow, citron yellow, yellow, orange, or light brown in varying intensities, depending on the origin, facies, degree of diagenesis, and direction of polished section. Coal facies can appear black or dark brown in color and can also have a duller appearance in comparison to silt. Coal facies can have sedimentary structures ranging from thin laminated structures to thick laminated structures and can include plant remains, such as stems, bark, and leaves. The degree of diagenesis can be related to hydrocarbon thermal maturation, and the degree of diagenesis can increase with an increase in bituminite reflectance and a decrease in fluorescence intensity. With respect to the direction of polished section, the polished section can be made in an orientation that is perpendicular to the bedding planes of a rock sample in which the intergranular features are well preserved.

Bituminite appears in various oil shales, especially of marine and lacustrine source rocks of kerogen type II and some coals. Bituminite can occur as autochthonous material, either as a fine, granular groundmass or as laminae, irregular streaks, wipes, threads, bands, or elongated lenses with a vein-like appearance, fine disseminations (as seen in perpendicular sections) or as homogenous, diffuse, equidimensional particles of various shapes (as seen in horizontal sections of lignite and bituminous coals and sedimentary rock). In reflected light, bituminite can appear dark gray, brown, or black. In some cases, bituminite is surrounded by mineral impurities, which can give rise to internal reflections in reflected light. Bituminite is derived from variable organic matter which underwent alteration, degradation, or both. Therefore, bituminite can exhibit varying intensities of fluorescence and sometimes exhibit no fluorescence. With increasing degree of diagenesis, bituminite reflectance can increase, and the fluorescence intensity of bituminite can decrease. In fluorescence, the color of bituminite can appear originally as yellow, and in some cases, shift gradually from yellow to orange to red with maturity. At vitrinite reflectance values of 0.8 to 0.9% $R_o$, fluorescence can be lost. Hydrocarbons can be generated from bituminite as it matures, which can result in leaving mostly dehydrogenated residual products.

In some cases, the presence of suppressed vitrinite can reduce vitrinite reflectance measurements and may create difficulties in assessing the thermal maturity of a sedimentary basin from which the rock sample 102 was obtained. Vitrinite suppression can occur due to various factors, such as high liptinite content, transgressive sequences containing marine deposits, presence of aliphatic lipids, presence of bitumens derived from liptinites, generation of perhydrous (hydrogen/aliphatic-rich) vitrinite in anaerobic depositional environments, generation of perhydrous vitrinite in alkaline depositional environments, and occurrence of hydrogen- and aliphatic-rich vitrinite originating from some types of flora. Vitrinite suppression can occur immediately after a sediment has been deposited and can continue to reduce the reflectance until the hydrogen/bitumen is removed from the structure. The occurrence of vitrinite suppression is related to specific organic facies and depositional environments. In some cases, vitrinite suppression is more likely to occur in shales and sandstones in comparison to coals.

To identify vitrinite suppression, various measures can be taken. For example, low vitrinite fluorescence of maximum intensity (red and green) can be measured. The variation of fluorescence (in color and/or intensity) can enable distinction among various organic and inorganic constituents in coals and bituminous shales. For example, liptinite fluorescence intensity can decrease with increasing maturity and exhibit a shift toward red fluorescence. Therefore, in some cases, a decrease in fluorescence intensity with increasing maturity can be correlated to a shift to longer wavelengths. For example, chlorophyllinite (when well preserved) can be identified by its red fluorescence.

As another example, the presence of liptinite including amorphous organic matter content (>20% by volume) can be detected. Some conditions under which vitrinite suppression can be recognized and predicted include transgressive sequences containing marine deposits, oxygen deficiency in alkaline deposition, presence of high liptinite content, and vitrinite formed from waxy, aliphatic-rich plants with oil-prone type III kerogen. The presence of liptinite with >20% by volume of amorphous organic matter content can produce vitrinite suppression. The concentration of liptinite macerals to produce vitrinite suppression can depend on the type of maceral present in the rock sample.

Based on the one or more maceral attributes determined at step 203 and the classification attributes recorded at step 201, one or more technical attributes of the photomicrograph are determined using automated face recognition at step 205. The one or more technical attributes can include thermal maturity, organic richness, mineral composition, or combinations of these. The results of the automated face detection at step 203 can be compared to various photomicrographs in a database. The comparison can be performed with photomicrographs which have overlap in the maceral attributes determined at step 203, the classification attributes recorded at step 201, or a combination of both.

The organic richness can be expressed as a weight percent (wt. %). The organic richness and maturity of potential source rocks can be verified in a separate analysis, for example, a pyrolysis or thermal oxidation analysis. In a pyrolysis analysis, the organic content of a rock sample can be pyrolyzed in the absence of oxygen and then combusted. The amount of hydrocarbons and carbon dioxide released can be measured to determine the organic richness. A commonly used pyrolysis technique is Rock-Eval pyrolysis. The organic richness (in wt. %) can be used to provide a general idea about the abundance of organic matter in a source rock, indicating the likelihood of the abundance of vitrinite (which can aid in the vitrinite reflectance measurement).

The automated face recognition can be used to reduce the duration of analysis and provide consistent and reliable interpretation of photomicrograph data. The automated face recognition can utilize the vast amounts of information already available in various databases and can also contribute information to the databases once analysis is complete. The automated face recognition can be combined with machine learning algorithms to improve accuracy of interpretation and analysis. Similarities and dissimilarities can be identified based on known maceral features and general attributes typical of photomicrographs.

At step 207, the one or more maceral attributes determined at step 203 and the one or more technical attributes determined at step 205 are provided to a user analyzing the rock sample 102. The attributes can be, for example, displayed on a monitor of the computer 500. In some implementations, the attributes are stored in a suitable persistent memory storage (for example, of the computer 500). In some implementations, the results of the method 200 are stored in sets corresponding to the one or more classification attributes of the photomicrograph. In some implementations, the results of the method 200 are stored in a database (for example, the database of photomicrographs), an offsite data repository, a separate local or remote database, or within a machine associated database. In some cases, it can be beneficial to store the results of the method 200 to the same database with which the attributes of the photomicrograph are compared.

Figure 3A:
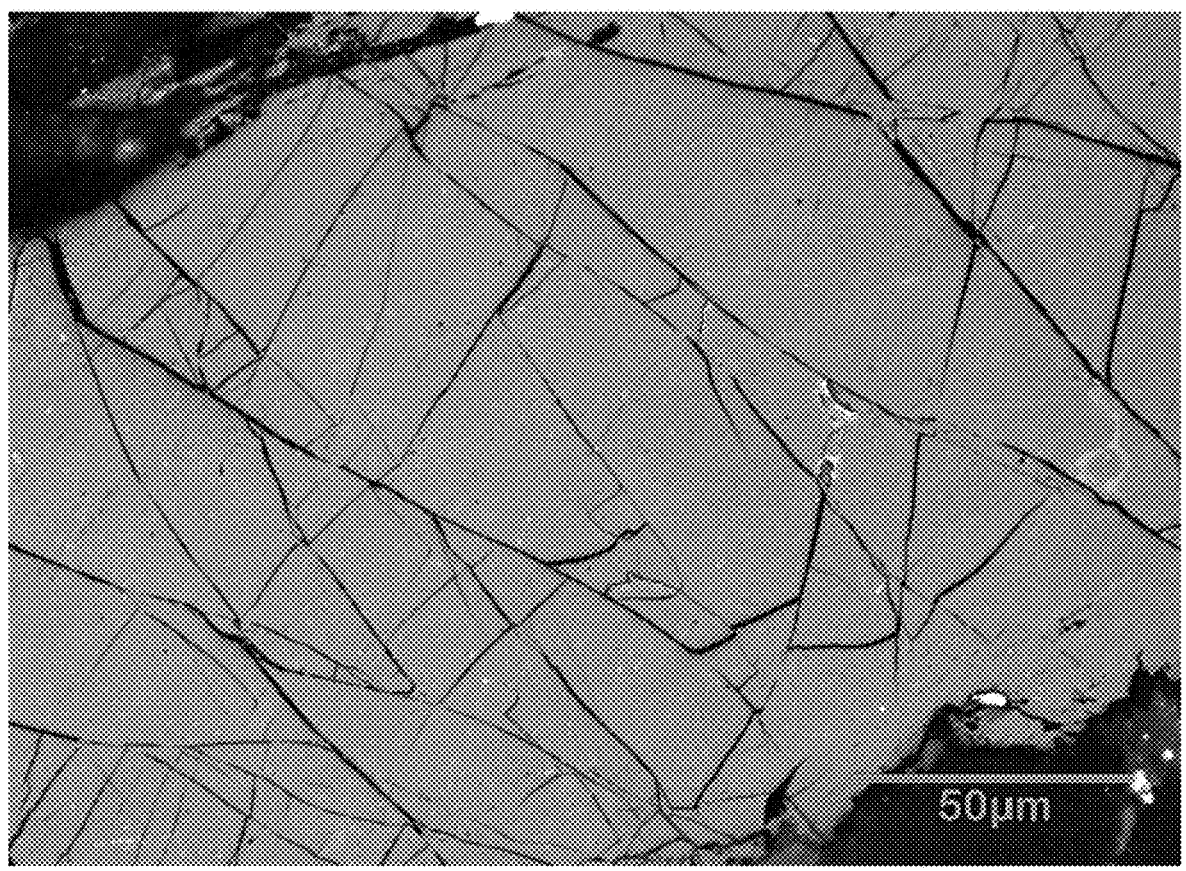
FIGS. 3AA, 3AB, 3B, and 3C are example photomicrographs.
Figure 3A:
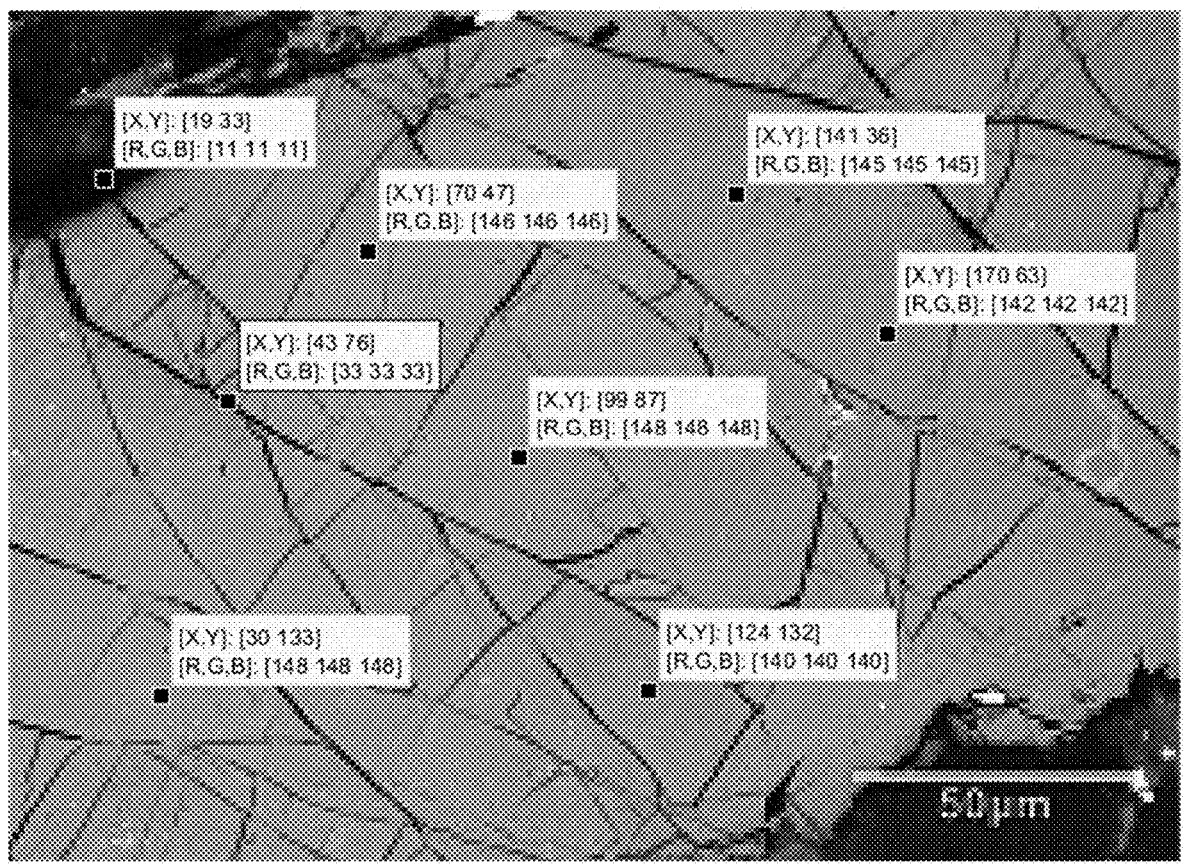
Figure 3B:
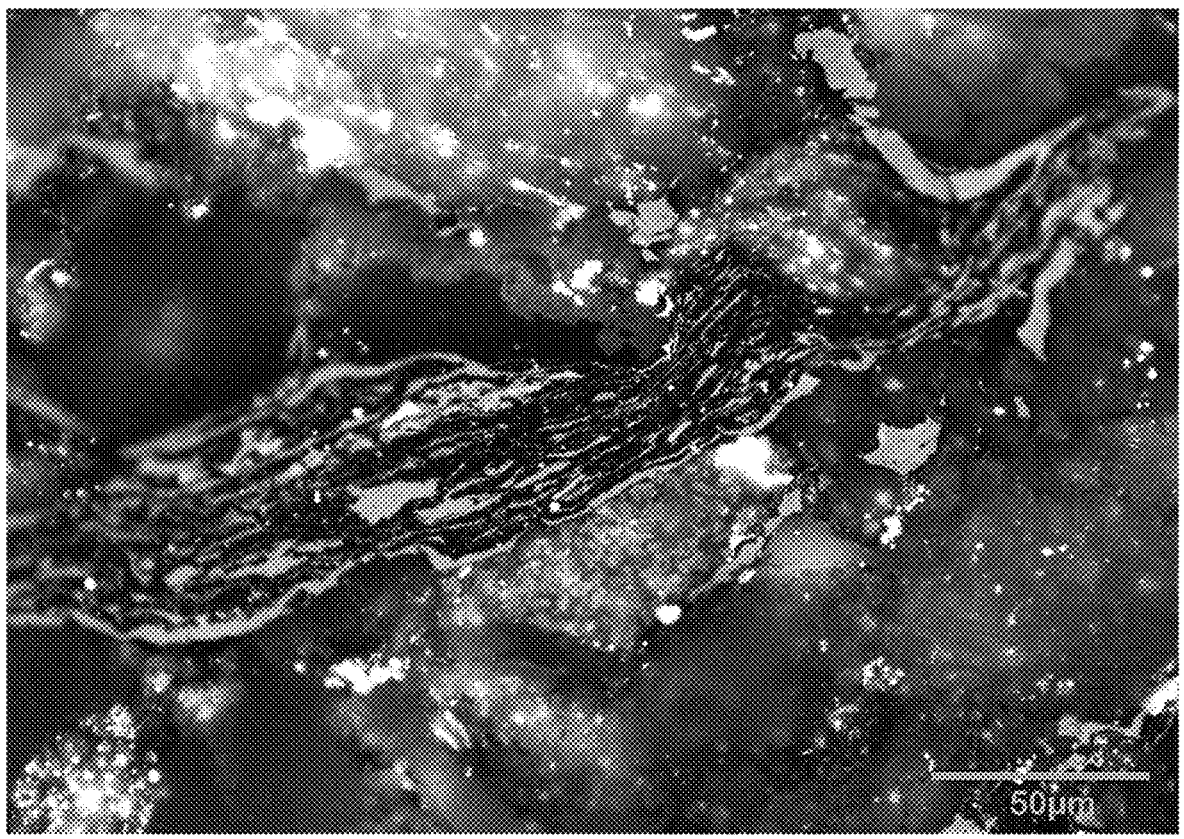
Figure 3C:
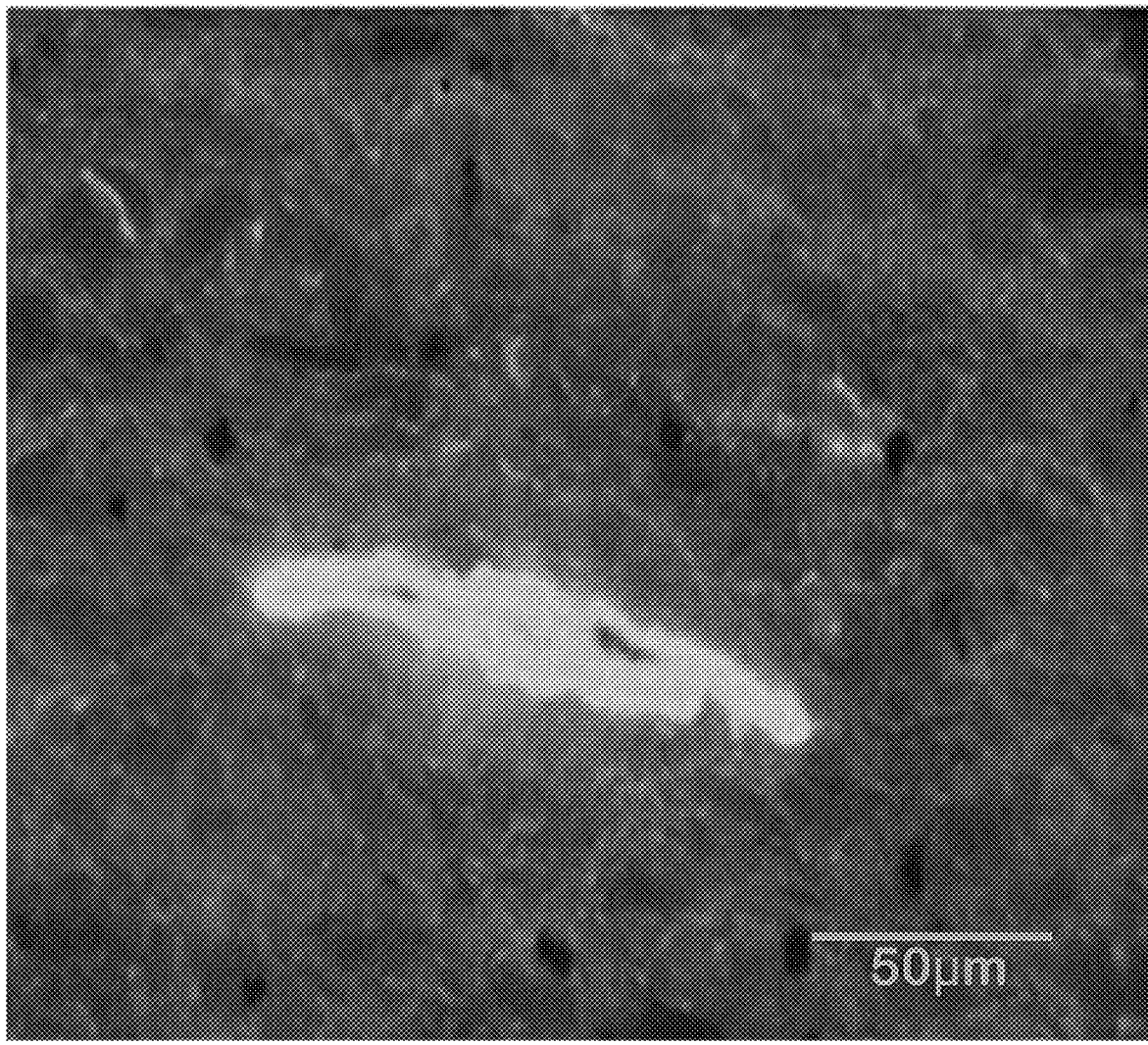

FIGS. 3AA, 3AB, 3B, and 3C show example photomicrographs (of various rock samples) that were obtained using a microscope (such as the microscope 150). FIG. 3AA is an example photomicrograph of a rock sample including vitrinite with microfractures. The measured vitrinite reflectance and the measured organic carbon content for the rock sample of FIG. 3AA was 1.8% $R_o$ and 3.5 weight %, respectively. FIG. 3AB shows the same photomicrograph as FIG. 3AA but with vitrinite readings (based on detected vitrinite reflectance) of various points. RGB values between 140 and 148 signify the presence of vitrinite, while lower RGB values (such as 11 and 33) signify non-vitrinite reflectance. FIG. 3B is an example photomicrograph of a rock sample including microfolded solid bitumen. The measured vitrinite reflectance and the measured organic carbon content for the rock sample of FIG. 3B was 1.8% $R_o$ and 1.8 weight %, respectively. FIG. 3C is an example photomicrograph of a rock sample including lamalginite and telalginite.

FIGS. 4A, 4B, 4C, 4D, 4E, 4F, 4G, 4H, and 4J show example photomicrographs (of various rock samples) that were obtained using a microscope (such as the microscope 150). Method 200 was implemented on these photomicrographs to identify attributes and classify the respective rock samples. Table 3 shows various attributes of the rock samples.

TABLE 3

| Figure | Country of Origin | Basin | Age | Depth (meters) | Lithology | Stratigraphic Unit |
|---|---|---|---|---|---|---|
| 4A | Germany | Rhenohercynian | Carboniferous | 68.5 | Shale | Upper Alum Shale |
| 4B | Scotland | Orcadian | Middle Devonian | Outcrop | Shale | Flagstone |
| 4C | Czech Republic | Vienna | Upper Jurassic | 4,277 | Marl | Mikulov |
| 4D | Germany | Rhenohercynian | Carboniferous | 89.4 | Shale | Ziegelschiefer |
| 4E | Scotland | Orcadian | Devonian | Outcrop | Shale | Flagstone |
| 4F | Czech Republic | Vienna | Upper Jurassic | 4,131 | Marl | Mikulov |
| 4G | Saudi Arabia | North West | Carboniferous | 1,000 | Shale | Berwath |
| 4H | Saudi Arabia | North West | Carboniferous | 1,000 | Shale | Berwath |
| 4J | Scotland | Orcadian | Middle Devonian | Outcrop | Shale | Flagstone |

Table 4 shows various attributes of the photomicrographs of the respective rock samples.

TABLE 4

Figure 4A:
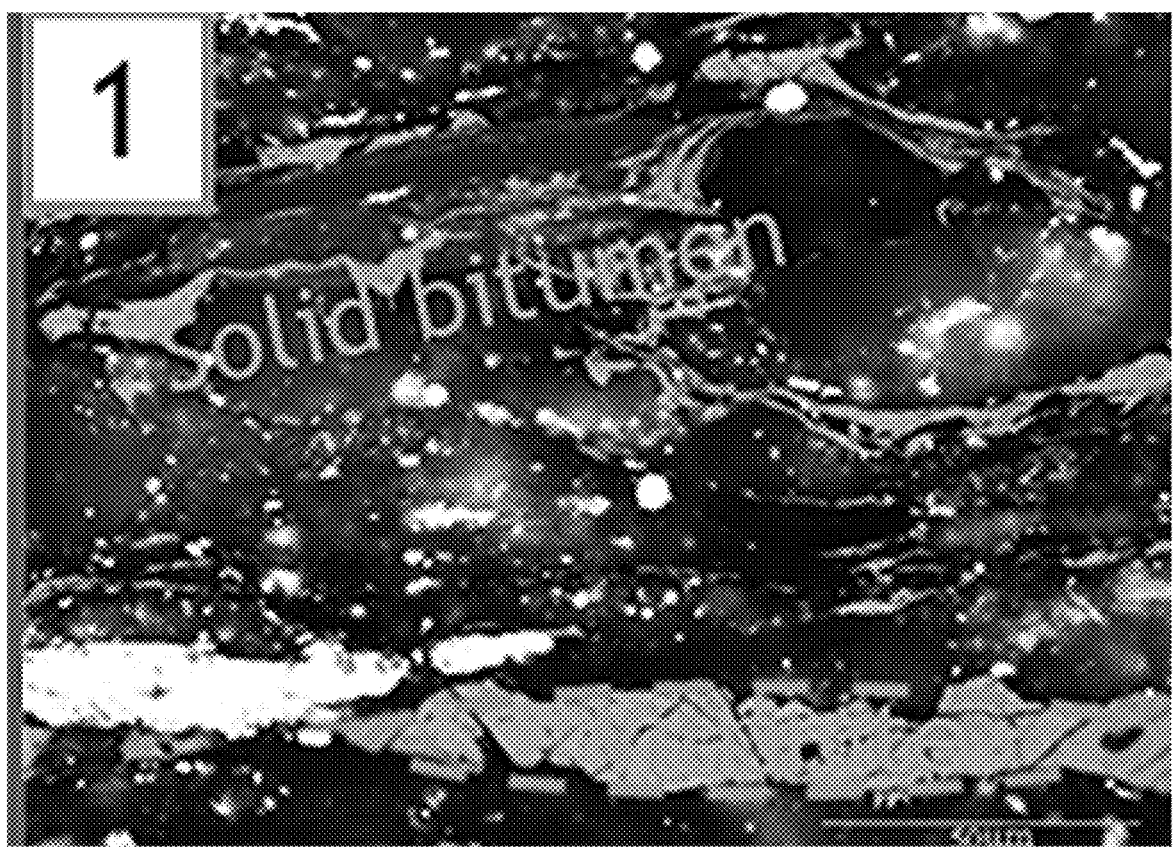
FIGS. 4A, 4B, 4C, 4D, 4E, 4F, 4G, 4H, 4JA, and 4JB are example photomicrographs.
Figure 4B:
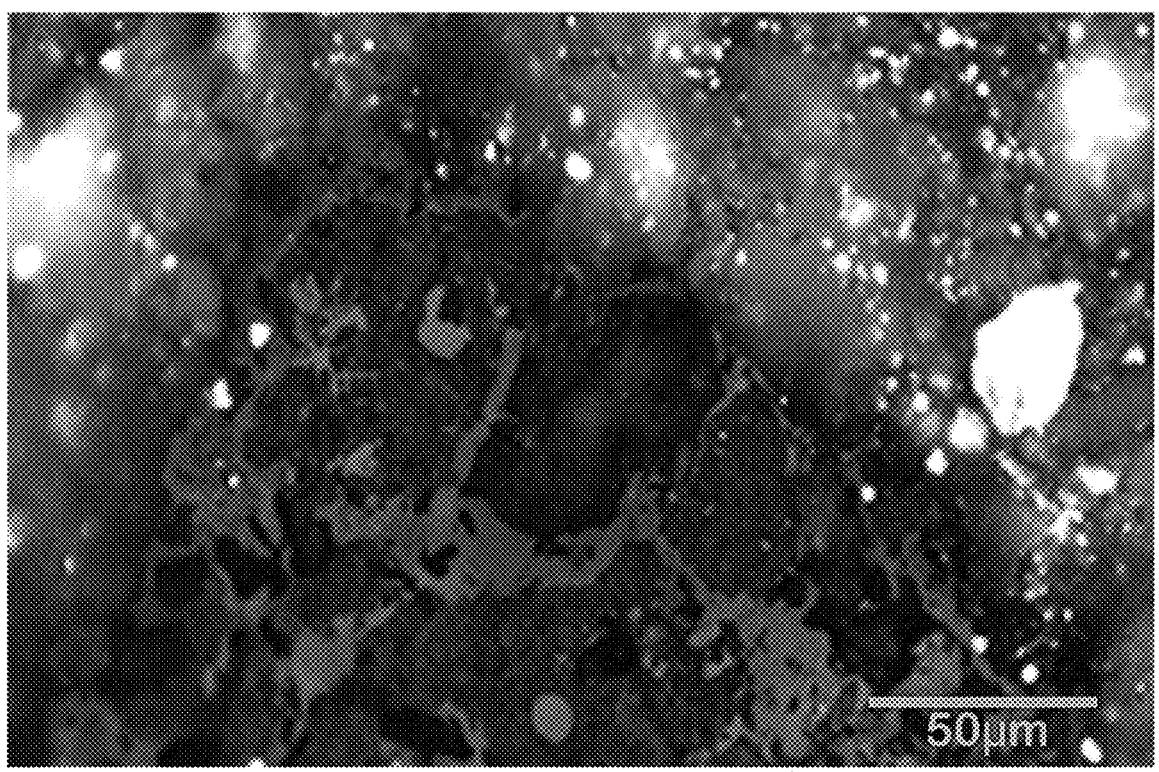
Figure 4C:
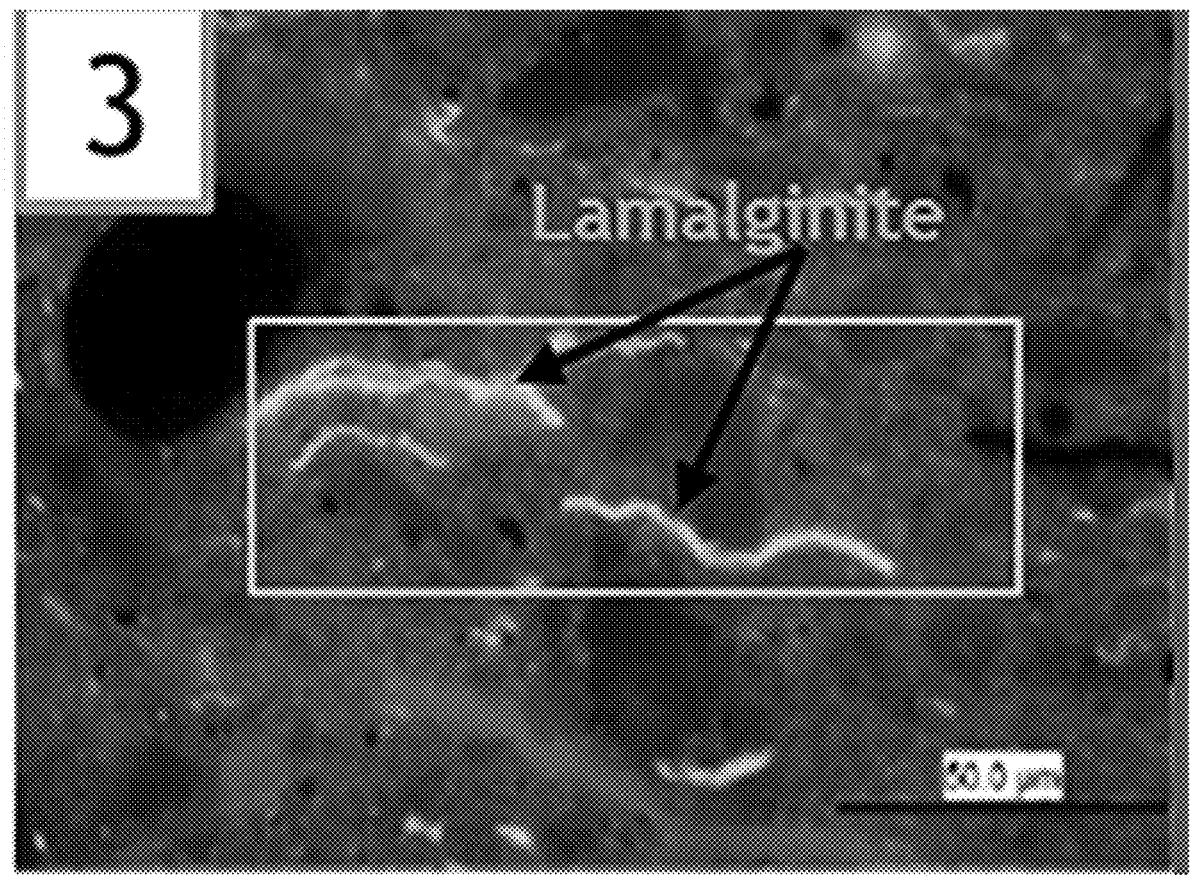
Figure 4D:
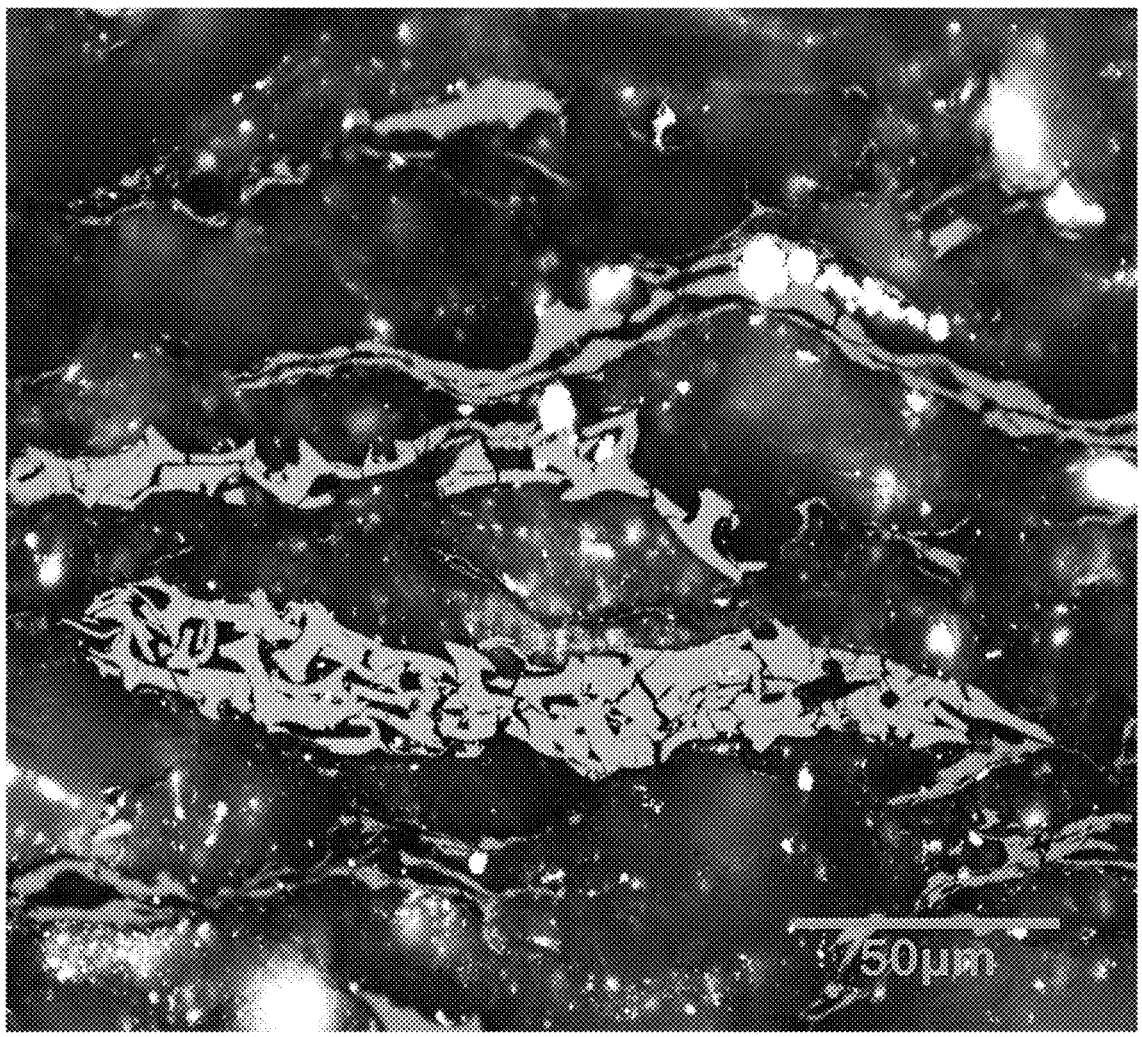
Figure 4E:
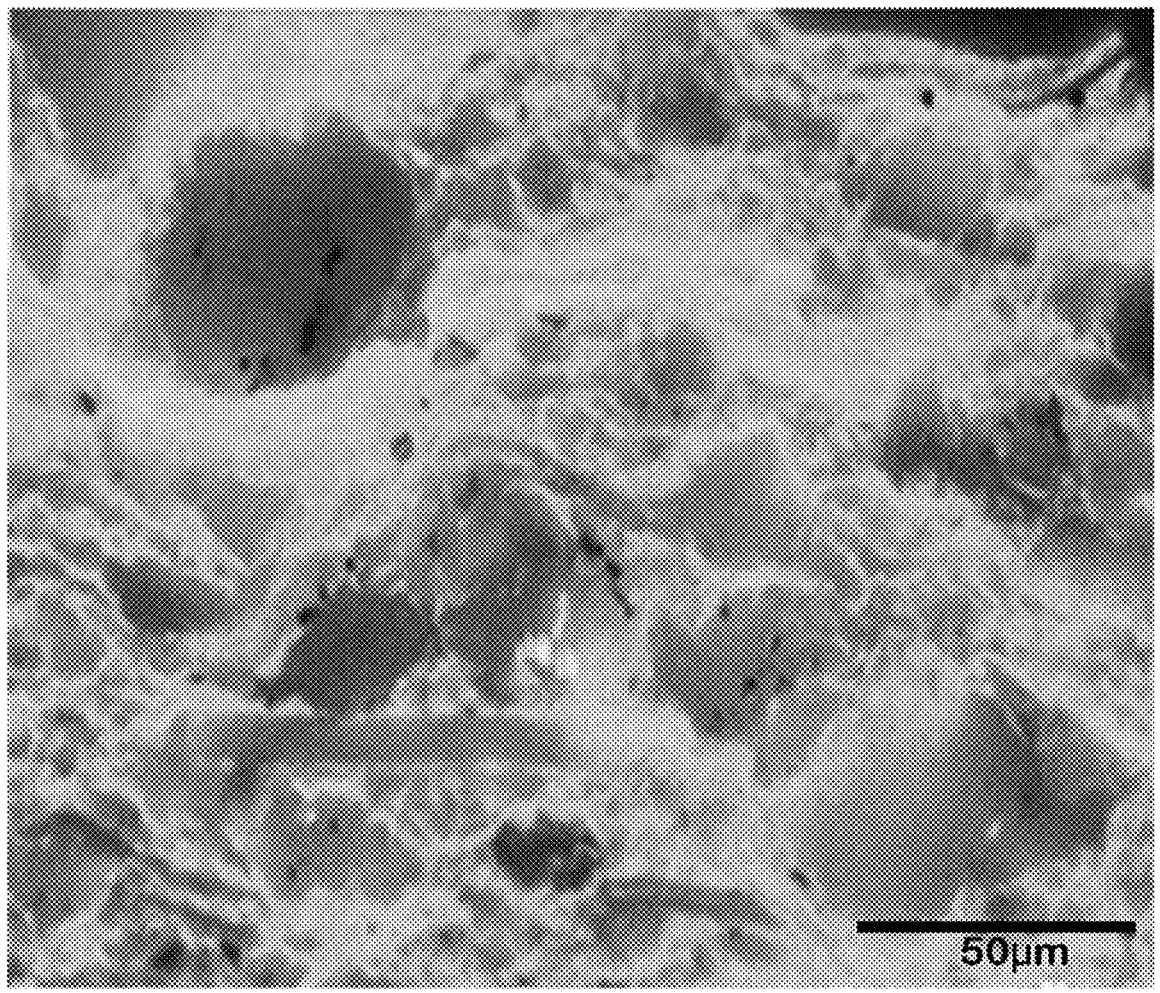
Figure 4F:
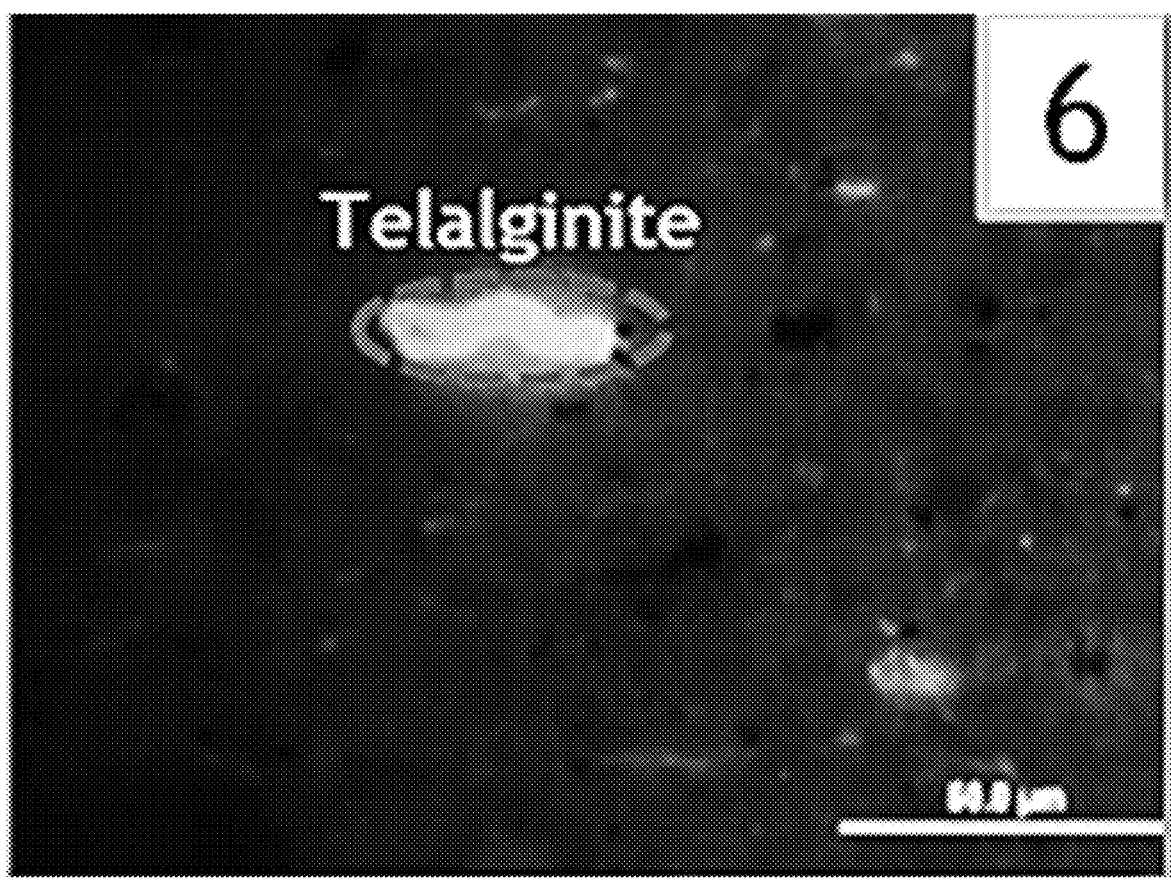
Figure 4G:
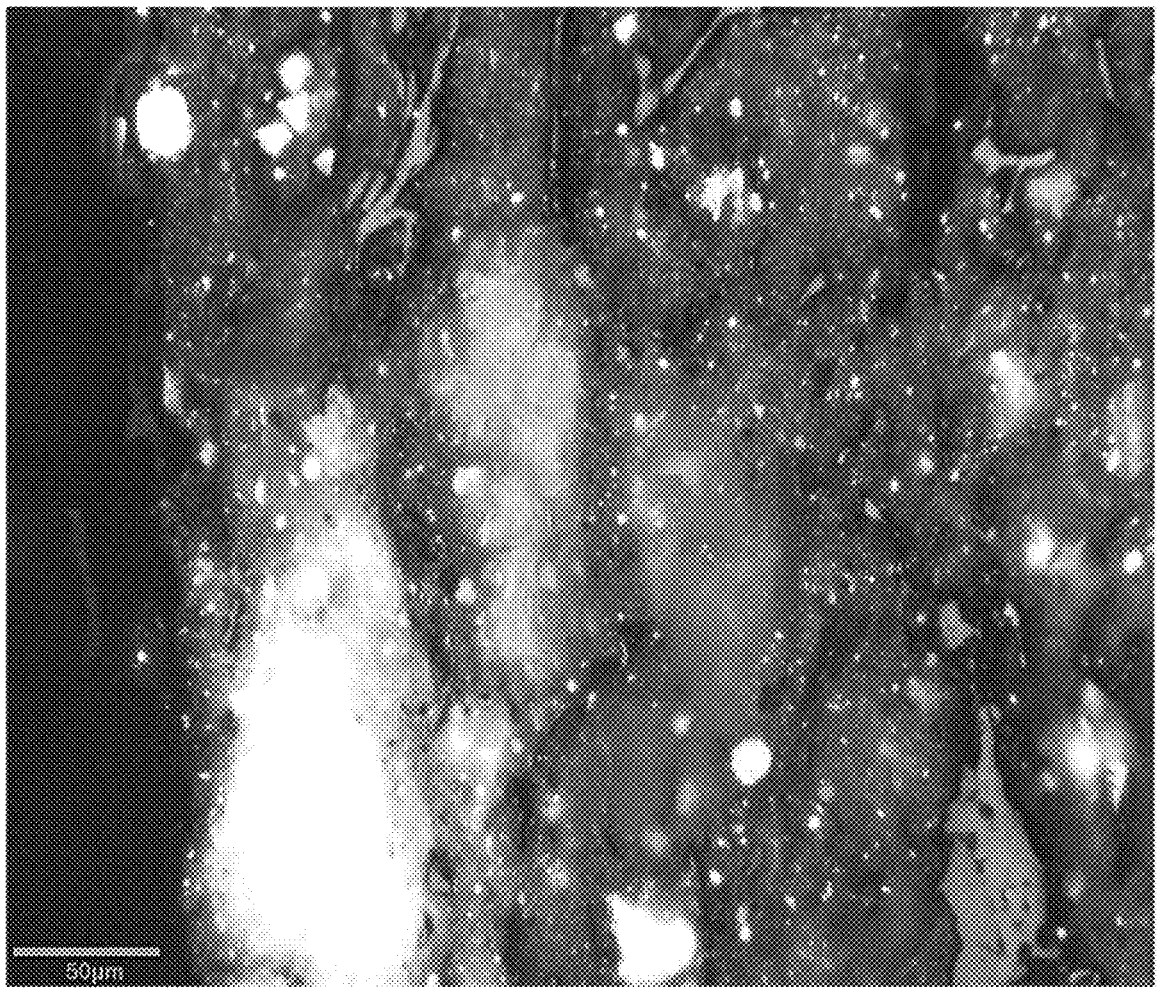
Figure 4H:
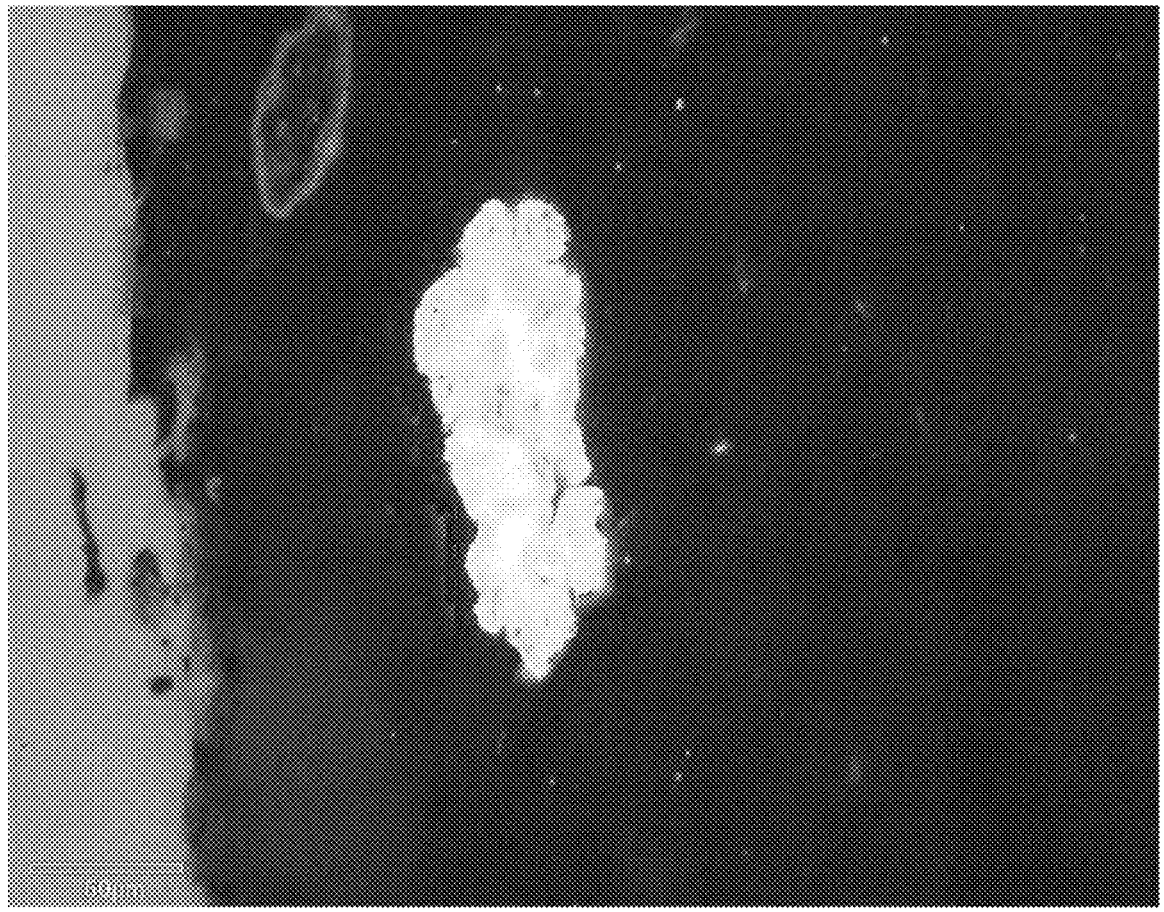
Figure 4J:
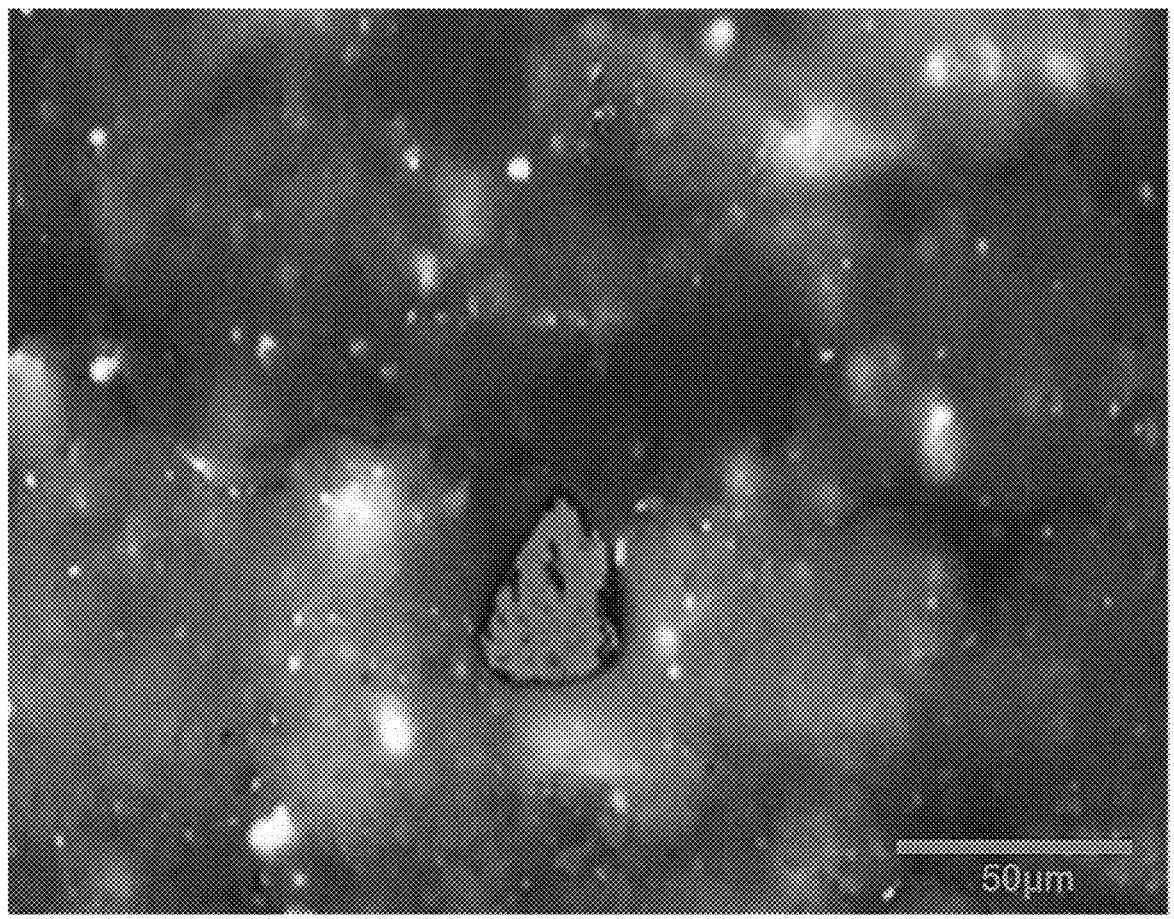
Figure 4J:
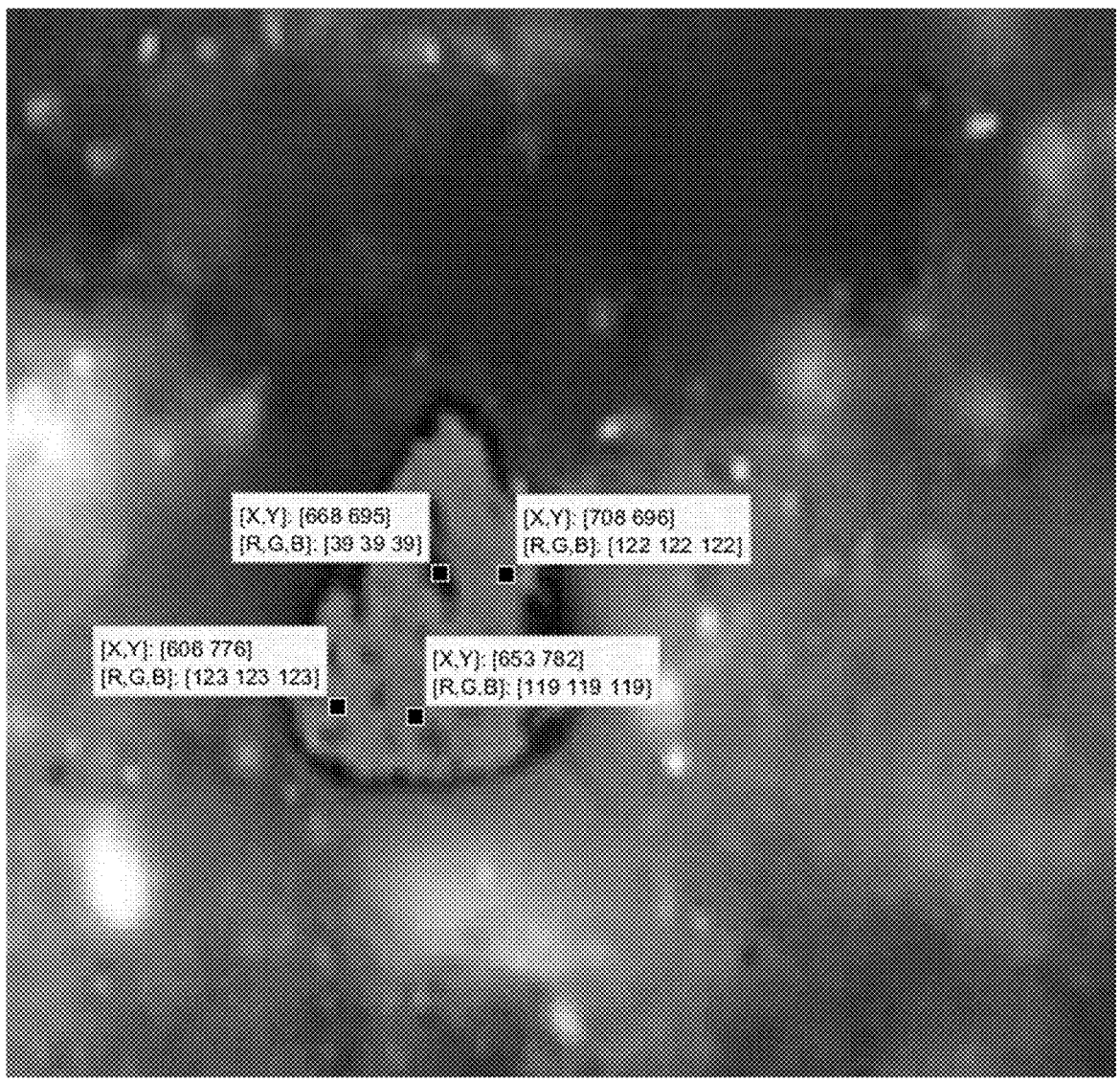

| Positive Vitrinite Presence | Incident White Light | Vitrinite Measurements Taken | Polarized Light | Fluorescence |
|---|---|---|---|---|
| FIG. 4A | FIG. 4A | FIG. 4A | FIG. 4G | FIG. 4C |
| FIG. 4G | FIG. 4B | FIG. 4D | | FIG. 4E |
| FIG. 4J | FIG. 4D | FIG. 4J | | FIG. 4F |
| | FIG. 4J | | | FIG. 4H |

In the photomicrograph of FIG. 4A, solid bitumen and vitrinite were positively identified by face detection and face recognition of method 200. In the photomicrograph of FIG. 4B, solid bitumen was positively identified by face detection and face recognition of method 200. In the photomicrograph of FIG. 4C, lamalginite was positively identified by face detection and face recognition of method 200. In the photomicrograph of FIG. 4D, pyrite framboids and fusinite were positively identified by face detection and face recognition of method 200. In the photomicrograph of FIG. 4E, telalginite and lamalginite were positively identified by face detection and face recognition of method 200. In the photomicrograph of FIG. 4F, telalginite was positively identified by face detection and face recognition of method 200. In the photomicrograph of FIG. 4G, pyrite, botryococcus, and vitrinite were positively identified by face detection and face recognition of method 200. In the photomicrograph of FIG. 4H, botryococcus was positively identified by face detection and face recognition of method 200. In the photomicrograph of FIG. 4JA, vitrinite was positively identified by face detection and face recognition of method 200. FIG. 4JB shows the same photomicrograph as FIG. 4JA but with vitrinite readings (based on detected vitrinite reflectance) of various points. The lower RGB values (such as 39) signify non-vitrinite reflectance, while the higher RGB values (such as greater than 100) indicate the presence of vitrinite.

The following expression can be used to calculate interval estimate based on the desired confidence level for a set of readings (for example, for vitrinite reflectance based on RGB values).

$$X \pm Z \frac{s}{\sqrt{n}}$$

where X is the mean, s is the standard deviation, n is the number of readings, and Z is defined based on the desired confidence level. The following table provides some example values for Z based on various desired confidence levels.

| Confidence Level | Z |
|---|---|
| 80% | 1.282 |
| 85% | 1.440 |
| 90% | 1.645 |
| 95% | 1.960 |
| 99% | 2.576 |
| 99.5% | 2.807 |
| 99.9% | 3.291 |

For example, for a set of 30 readings (n), the mean (X) was 144.8, and the standard deviation (n) was 8. For a desired confidence level of 99.9% (Z=3.291), the interval estimate was 140 to 150.

Figure 5:
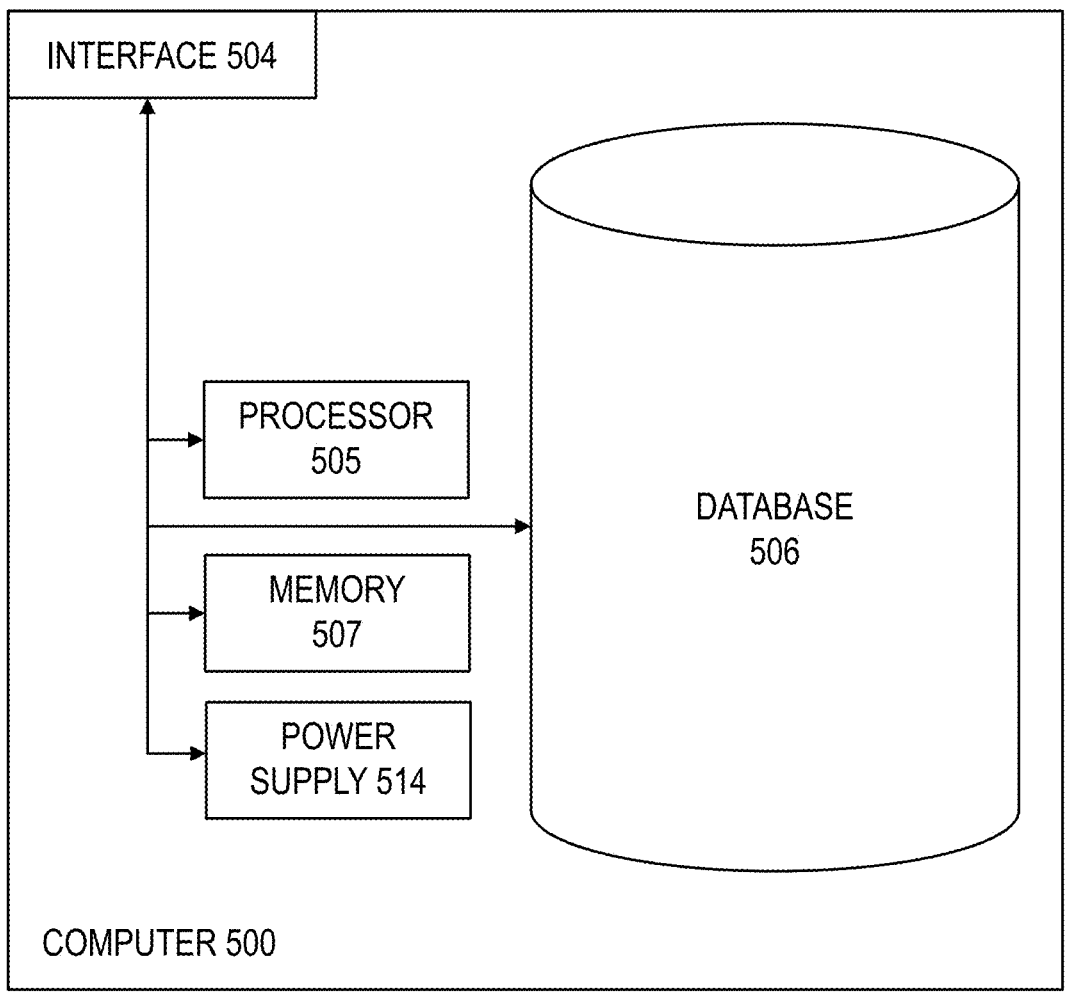
FIG. 5 is a block diagram of an exemplary computer of the system of FIG. 1.

FIG. 5 is a block diagram of an example computer 500 used to provide computational functionalities associated with described algorithms, methods, functions, processes, flows, and procedures, as described in this specification, according to an implementation. The illustrated computer 500 is intended to encompass any computing device such as a server, desktop computer, laptop/notebook computer, one or more processors within these devices, or any other suitable processing device, including physical or virtual instances (or both) of the computing device. Additionally, the computer 500 can include a computer that includes an input device, such as a keypad, keyboard, touch screen, or other device that can accept user information, and an output device that conveys information associated with the operation of the computer 500, including digital data, visual, audio information, or a combination of information.

The computer 500 includes a processor 505. Although illustrated as a single processor 505 in FIG. 5, two or more processors may be used according to particular needs, desires, or particular implementations of the computer 500. Generally, the processor 505 executes instructions and manipulates data to perform the operations of the computer 500 and any algorithms, methods, functions, processes, flows, and procedures as described in this specification.

The computer 500 can also include a database 306 that can hold data for the computer 500 or other components (or a combination of both) that can be connected to the network. Although illustrated as a single database 506 in FIG. 5, two or more databases (of the same or combination of types) can be used according to particular needs, desires, or particular implementations of the computer 500 and the described functionality. While database 506 is illustrated as an integral component of the computer 500, database 506 can be external to the computer 500.

The computer 500 also includes a memory 507 that can hold data for the computer 500 or other components (or a combination of both) that can be connected to the network. Although illustrated as a single memory 507 in FIG. 5, two or more memories 507 (of the same or combination of types) can be used according to particular needs, desires, or particular implementations of the computer 500 and the described functionality. While memory 307 is illustrated as an integral component of the computer 500, memory 507 can be external to the computer 500. The memory 507 can be a transitory or non-transitory storage medium.

The memory 507 stores computer-readable instructions executable by the processor 505 that, when executed, cause the processor 505 to perform operations, such as controlling the camera of the microscope 150, performing the automated face detection at step 203, and performing the automated face recognition at step 205. The computer 500 can also include a power supply 514. The power supply 514 can include a rechargeable or non-rechargeable battery that can be configured to be either user- or non-user-replaceable. The power supply 514 can be hard-wired. There may be any number of computers 500 associated with, or external to, a computer system containing computer 500, each computer 500 communicating over the network. Further, the term "client," "user," "operator," and other appropriate terminology may be used interchangeably, as appropriate, without departing from the scope of this specification. Moreover, this specification contemplates that many users may use one computer 500, or that one user may use multiple computers 500.

In this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In this disclosure, "approximately" means a deviation or allowance of up to 10 percent (%) and any variation from a mentioned value is within the tolerance limits of any machinery used to manufacture the part.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise. "About" can allow for a degree of variability in a value or range, for example, within 10%, within 5%, or within 1% of a stated value or of a stated limit of a range.

While this disclosure contains many specific implementation details, these should not be construed as limitations on the scope of the subject matter or on the scope of what may be claimed, but rather as descriptions of features that may be specific to particular implementations. Certain features that are described in this disclosure in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example implementations do not define or constrain this disclosure. Other changes, substitutions, and alterations are also possible without departing from the spirit and scope of this disclosure.

What is claimed is:

1. A method comprising:
   recording one or more classification attributes of a photomicrograph of a rock sample, wherein the one or more classification attributes comprise region of origin, basin, age, depth, lithology, stratigraphic unit, standard of preparation, or combinations thereof;
   determining one or more maceral attributes of the photomicrograph using automated face detection, wherein determining the one or more maceral attributes of the photomicrograph comprises measuring a vitrinite reflectance of the photomicrograph to determine a presence of vitrinite in the rock sample and determining whether vitrinite suppression has occurred in the rock sample;
   based on the one or more classification attributes and the one or more maceral attributes, determining one or more technical attributes of the photomicrograph using automated face recognition, wherein the one or more technical attributes comprise thermal maturity, organic richness, mineral composition, or combinations thereof, wherein determining the one or more technical attributes comprises comparing results of the automated face detection to a database of photomicrographs with overlap in one or more classification attributes; and
   providing the one or more maceral attributes and the one or more technical attributes.

2. The method of claim 1, wherein the photomicrograph comprises an incident light photomicrograph of the rock sample.

3. The method of claim 2, comprising obtaining the incident light photomicrograph of the rock sample.

4. The method of claim 1, wherein the photomicrograph of the rock sample is a set of photomicrographs of the rock sample, the set comprising an incident light photomicrograph of the rock sample and a fluorescent photomicrograph of the rock sample.

5. The method of claim 4, comprising obtaining the fluorescent photomicrograph of the rock sample in response to determining that vitrinite suppression has occurred in the rock sample.

6. The method of claim 5, comprising determining a presence of macerals other than vitrinite in the rock sample using automated face detection on the fluorescent photomicrograph.

7. The method of claim 1, comprising measuring a total organic content in weight percent of the rock sample.

8. The method of claim 7, wherein determining the one or more technical attributes of the photomicrograph comprises identifying one or more minerals that make up the total organic content of the rock sample.

9. A system for automated organic petrology, the system comprising:
   a memory; and
   a hardware processor interoperably coupled with the memory and configured to:
      record one or more classification attributes of a photomicrograph of a rock sample, wherein the one or more classification attributes comprise region of origin, basin, age, depth, lithology, stratigraphic unit, standard of preparation, or combinations thereof;
      determine one or more maceral attributes of the photomicrograph using automated face detection, wherein determining the one or more maceral attributes of the photomicrograph comprises measuring a vitrinite reflectance of the photomicrograph to determine a presence of vitrinite in the rock sample and determining whether vitrinite suppression has occurred in the rock sample;
      based on the one or more classification attributes and the one or more maceral attributes, determine one or more technical attributes of the photomicrograph using automated face recognition, wherein the one or more technical attributes comprise thermal maturity, organic richness, mineral composition, or combinations thereof, wherein determining the one or more technical attributes comprises comparing results of the automated face detection to a database of photomicrographs with overlap in classification attributes; and providing the one or more maceral attributes and the one or more technical attributes.

10. The system of claim 9, wherein the hardware processor is configured to obtain an incident light photomicrograph of the rock sample.

11. The system of claim 9, wherein the hardware processor is configured to obtain a fluorescent photomicrograph of the rock sample in response to determining that vitrinite suppression has occurred in the rock sample.

12. The system of claim 11, wherein the hardware processor is configured to determine a presence of macerals other than vitrinite in the rock sample using automated face detection on the fluorescent photomicrograph.

13. The system of claim 9, wherein the hardware processor is configured to measure a total organic content in weight percent of the rock sample.

14. The system of claim 13, wherein the hardware processor is configured to identify one or more minerals that make up the total organic content of the rock sample.

* * * * *